(12) United States Patent
Makuska (10) Patent No.: US 7,799,194 B2
(45) Date of Patent: Sep. 21, 2010

(54) ELECTROPHORETIC GELS AND THEIR MANUFACTURE

(75) Inventor: Ricardas Makuska, Vilnius (LT)

(73) Assignee: Fermentas UAB, Vilnius (LT)

( * ) Notice: Subject to any disclaimer, the term of this patent is extended or adjusted under 35 U.S.C. 154(b) by 1649 days.

(21) Appl. No.: 10/893,013

(22) Filed: Jul. 16, 2004

(65) Prior Publication Data

US 2008/0029392 A1 Feb. 7, 2008

(30) Foreign Application Priority Data

Jul. 17, 2003 (GB) .................................. 0316742.6

(51) Int. Cl.

| | |
|---|---|
| G01N 33/559 | (2006.01) |
| B01D 57/02 | (2006.01) |
| B01D 59/42 | (2006.01) |
| B01D 59/50 | (2006.01) |
| B01D 61/42 | (2006.01) |
| B01D 61/58 | (2006.01) |
| C02F 1/469 | (2006.01) |
| C07K 1/26 | (2006.01) |
| C08F 2/58 | (2006.01) |
| C25B 7/00 | (2006.01) |
| C25B 15/00 | (2006.01) |
| G01F 1/64 | (2006.01) |

(52) U.S. Cl. ........................ 204/469; 204/470; 204/456

(58) Field of Classification Search ................ 204/469, 204/470, 456

See application file for complete search history.

(56) References Cited

U.S. PATENT DOCUMENTS

| | | | |
|---|---|---|---|
| 2,922,786 A | 1/1960 | Mino et al. | |
| 3,507,851 A | 4/1970 | Ghetie et al. | |
| 3,728,151 A * | 4/1973 | Sherman et al. ............... 442/80 |
| 3,860,573 A | 1/1975 | Honkanen et al. | |
| 3,956,272 A | 5/1976 | Tixier | |
| 3,956,273 A | 5/1976 | Guiseley | |
| 3,959,251 A | 5/1976 | Porath et al. | |
| 4,319,975 A | 3/1982 | Cook | |
| 4,756,834 A | 7/1988 | Muller et al. | |
| 5,135,627 A | 8/1992 | Soane | |
| 5,143,646 A | 9/1992 | Nochumson et al. | |
| 5,230,832 A | 7/1993 | Perlman | |
| 5,290,411 A | 3/1994 | Zewert et al. | |
| 5,321,357 A | 6/1994 | Maryanski et al. | |
| 5,541,255 A | 7/1996 | Kozulic | |
| 5,658,561 A | 8/1997 | Nakabayashi et al. | |
| 5,674,946 A | 10/1997 | Muller | |
| 5,840,877 A | 11/1998 | Kozulic | |
| 5,883,211 A | 3/1999 | Sassi et al. | |
| 6,291,216 B1 | 9/2001 | Muller et al. | |
| 7,288,373 B2 * | 10/2007 | Millar et al. .................... 435/6 |

FOREIGN PATENT DOCUMENTS

| | | |
|---|---|---|
| EP | 0 117478 | 9/1984 |
| GB | 1352613 | 5/1974 |
| GB | 1600241 | 10/1981 |
| WO | WO92/15868 | 9/1992 |
| WO | WO00/77059 | 12/2000 |
| WO | WO01/29098 | 4/2001 |

OTHER PUBLICATIONS

Mishra, A., Rajani, S., Agarwal, M., Dubey, R. (2002) P. psyllium-g-polyacrylamide: Synthesis and characterization; Polymer Bulletin, v. 48, p. 439-444.*
Uyama, Y., Kato, K., Ikada, Y. (1998) Surface Modification of Polymers by Grafting. Advances in Polymer Science, vol. 137, p. 1-39.*
Qiu, Y.X., Klee, D., Plüster, W., Severich, B., Höcker, H. (1996) Surface Modification of Polyurethane by Plasma-Induced Graft Polymerization of Poly(ethylene glycol) Methacrylate. Journal of Applied Polymer Science, vol. 61, p. 2373-2382.*
Athawale (2000) J. Polym. Mater. 17:1-7.
Athawale et al. (1999) European Polymer Journal 35:1237-1243.
Bode (1976) FEBS Letters 65:56-58.
Dumais et al. (1987) BioTechniques 5:62-67.
Fanta (1973) Block and Graft Copolymers, 1:1-45, R.J. Ceresa, ed., John Wiley and Sons, London.
Fanta (1966) Journal of Applied Polymer Science, 10:929-937.
Halab-Kessira et al. (1999) European Polymer Journal 35:1065-1071.
Horowitz et al. (1984) Analytical Biochemistry 143:333-340.
Mino et al. (1958) Journal of Polymer Science 31:242-243Odian et al. (1970) J. Macromol. Sci.-Chem. A4(2):317-330.
Oman et al. (1977) Analytical Biochemistry 83:211-215.
Porath et al. (1975) Journal of Chromatography 103:49-62.
Hans-Joachim Bode, "The Use of Liquid Polyacrylamide in Electrophoresis," Analytical Biochemistry 83, 204-210 (1977).

* cited by examiner

*Primary Examiner*—Shaojia Anna Jiang
*Assistant Examiner*—Scarlett Goon
(74) *Attorney, Agent, or Firm*—Crowell & Moring LLP (57) ABSTRACT

The invention relates to a method of preparing a gel for use in electrophoresis, which method comprises:

(a) providing a mixture comprising a solvent, agarose or a derivative thereof, one or more vinyl monomers, and a polymerisation initiator, the initiator forming a redox system with agarose or the derivative thereof;

(b) exposing the mixture to polymerisation conditions to graft-polymerise the one or more monomers onto the agarose or derivative thereof; and (c) allowing the mixture to form a gel.

59 Claims, 6 Drawing Sheets

ELECTROPHORETIC GELS AND THEIR MANUFACTURE

FIELD OF THE INVENTION

The present invention relates to electrophoretic gels. More particularly, the present invention relates to electrophoretic resolving gels with improved working properties and enhanced durability, and to a process for making thereof. The present invention also provides a graft polymer that can be used in making electrophoretic gels.

BACKGROUND IN THE ART

Electrophoresis is a process for separation of charged molecules and exploits the different mobility of molecules in an electric field. The mobility of molecules in an electric field depends on several factors such as the electrophoretic medium, the electric field strength and the characteristics of molecules (ions) themselves, such as size, shape and charge density. Electrophoresis is primarily used for the separation of biological macromolecules, such as proteins, nucleic acids and their derivatives. The process is usually carried out by forcing the molecules to migrate through a gel-supporting medium, the latter serving as a molecular sieve that enhances separation. The gel may be composed of natural or synthetic polymers. Agarose is the most widely used natural material and polyacrylamide gels represent the most common synthetic matrix. The gel may be immersed in a buffer, which serves as a conductive medium between electrodes and the gel. This format is known as submerged gel electrophoresis and it is the simplest to operate. Submerged gel electrophoresis is widely used for the analysis of nucleic acids.

Gels for electrophoresis can be prepared by free radical polymerization, by thermally induced gelation, and by a cross-linking reaction taking place simultaneously with gelation. Each of the three processes is currently being used for the production of precast gels for electrophoresis. Precast electrophoresis gels are manufactured by outside vendors, and are then shipped to the laboratory where the electrophoresis will be performed. Precast gels must have the required properties for electrophoresis and they must be able to maintain these properties throughout shipping and storage. The shelf life of many precast gels is limited by the potential for hydrolysis of acrylamide and/or buffer constitution during storage at the high pH of the gel buffer. Neutral buffer systems reduce degradation of polyacrylamide gels by hydrolysis, thereby increasing the useful shelf life of precast gels, as well as increasing the stability of the gels during electrophoresis. However, neutral gel systems suffer the disadvantage of providing lower separation and/or resolution.

Cross-linked polyacrylamide, produced by polymerizing acrylamide containing a few percent of N,N'-methylenebisacrylamide, is extensively employed as the matrix for gel electrophoresis. This is due primarily to the properties of the polymer, namely: excellent mechanical strength, adherence to glass surfaces, and a pore size which is controllable over a wide range. Polyacrylamide gels provide for high resolution of small sized sample components, e.g. they are capable of providing high resolution of DNA ranging in size from 6 to 1000 bp in length. Other advantages of cross-linked polyacrylamide gels are that they are optically transparent, providing for easy identification of separated sample components, they do not bind charged analytes, and they do not engender electroosmotic flow.

There are, however, certain properties of cross-linked polyacrylamide, which detract from its application as an electrophoretic medium. A major problem is that the cross-linked polyacrylamide gel must be prepared in situ, i.e., directly in an electrophoresis chamber utilizing free radical polymerization. Free radical reactions depend on a variety of parameters such as concentration of initiator, monomer purity, temperature, time, and absence of oxygen and other inhibitors. Managing these factors can require an inordinate amount of care and attention in order to achieve reproducible results. Another disadvantage associated with cross-linked polyacrylamide is the possible health hazard from handling the precursor monomers, acrylamide having been found to be a neurotoxin. A further disadvantage is that polyacrylamide gels are subject to degradation by hydrolysis and have a limited shelf life. In this regard, polyacrylamide gels are usually poured and run at basic pH. Hydrolysis of polyacrylamide at basic pH proceeds even at low temperature and the carboxylic groups formed are incorporated into the polymer, thus generating unwanted electro-endosmosis during electrophoresis.

Over the past two decades, a great deal of effort has been expended in the investigation and development of electrophoretic gel systems, which are free of the problems associated with polyacrylamide. In this regard, the use of agarose, a polysaccharide, showed considerable promise in the field of electrophoresis. Agarose gels, which comprise a natural, substantially linear, alternating copolymer of beta-D-galactose and 3,6-anhydro-alpha-L-galactose in an electrophoresis buffer, have many advantages in electrophoresis. They are thermoreversible, i.e. they undergo a transition from a first flowable state to second gel state in response to a change in temperature, thereby enabling separated components to be recovered from the melted gel. Agarose gels are also easy to prepare since they do not require free radical polymerization for gel formation. Furthermore, agarose is non-toxic, has a low susceptibility to electro-endoosmosis and has a high mechanical gel strength, providing for ease of manipulation. Gels prepared with native agarose exhibit a characteristic coarse pore structure, a feature that renders them the preferred medium for the electrophoretic separation of large macromolecules. Agarose gels comprising about 0.6 to 1 percent polymer are suitable primarily for the separation of proteins having molecular weights in excess of about 500,000 (500 kD) and DNA molecules in the size range from a few hundred to a few tens of thousand base pairs.

Despite these advantages, there are a number of disadvantages associated with the use of agarose gels in electrophoretic separation media. Smaller DNA molecules require higher agarose concentrations for good resolution, as generally known in the prior art. However, more concentrated agarose gels are difficult to prepare due to the resulting high viscosity of the agarose solutions. Furthermore, visualization of separated bands is difficult due to gel opacity.

It is known from the prior art that a gel of a particular composition and of a certain total concentration gives optimal resolution of macromolecules only in a limited size range. It is general knowledge in the art that outside a certain size range the resolution will be poor. Smaller molecules will give broad bands, whereas larger ones will not migrate sufficiently to be separated in a meaningful running time. Thus, the resolving power in the lower size range is limited by separation efficiency, and in the upper size range by separation selectivity. The resolving power of a gel can be improved by enhancing the efficiency or selectivity, or both.

The large pore limitation of agarose gels can be diminished and their sieving action improved by forming the gels from certain agarose derivatives having a finer pore structure than the parent agarose. U.S. Pat. No. 3,956,273 to Guisely and U.S. Pat. No. 4,319,975 to Cook disclose many derivatized agarose polymers. Although the majority of reagents used for derivatization were monofunctional, a bifunctional reagent could also be used. However, Guisely teaches that the ratio of the bifunctional reagent to agarose, as well as derivatization conditions, must be such that the polymer chains are not cross-linked, since otherwise the resulting product could not be re-dissolved, as required for a subsequent preparation of the electrophoresis gel. One preferred class of such modified agarose is hydroxyalkylated agarose produced by replacing hydroxyl groups 1 to 4 in the agarobiose units of the agarose polymer chain with hydroxyalkyl moieties.

A preferred member of this class, hydroxyethylated agarose, is obtained by reacting agarose with 2-chloroethanol in the presence of alkali. Gels formed from hydroxyethylated agarose are capable of resolving proteins from about 50 kD to about 600 kD. Moreover, such gels have lower melting points than native agarose gels, an advantage when recovering sensitive biological substances from the re-melted gels. Derivatization of hydroxyl groups of agarose, as disclosed in U.S. Pat. No. 3,956,273, reduces viscosity of agarose solutions, as well as gel opacity. Such hydroxyethylated agarose derivatives are commercially available products known under the trade name SeaPlaque (RTM) and NuSieve (RTM) (FMC Corporation). NuSieve (RTM) agarose that contains partially depolymerized hydroxyalkylagarose is typically used at polymer concentrations from about 2 to 8%, and improved resolution of small DNA using this agarose has been reported [Dumais and Nochumson, Bio Techniques, 5 (1987) 62]. However, separated DNA bands were bent (WO 92/15868 to Kozulic). The bending could be reduced by adjustment of ionic composition of the gel. However, it would be preferable to have a gel that does not require such an adjustment.

An aqueous electrophoretic resolving gel composition comprising two polysaccharide hydrogels, at least one of which has been derivatized, and independently, at least one of which has been partially de-polymerized sufficiently to reduce the casting-effective viscosity of the gel composition, has been proposed (U.S. Pat. No. 5,143,646 to Nochumson). In the preferred embodiment of the invention, component 1 of the resolving gel was partially de-polymerized hydroxyalkylated agarose while component 2 was a 1,2-dihydroxypropyl derivative of agarose (glycerated agarose). Some loss of sieving efficiency was incurred by the de-polymerized resolving gel component but this was compensated by the presence of a non-depolymerized component. The total amount of the two polysaccharides in the resolving gel was 4 to 8 wt. %. The gel system of this invention afforded separation of proteins in the molecular weight range of 10 to 200 kD with good resolution of individual protein bands, moderate viscosity for easy handling and melting of the gels at low temperature for easy sample recovery.

Bands representing separated species are bent in a submerged electrophoresis gel containing a high polymer concentration and the same buffer as the running buffer. The bending effect is related largely to the resistance of polymer chains to migration of buffer ions and is also possibly due to a change of relative migration rates of ions in the gel and buffer. The resistance may be reduced by lowering the polymer concentration of the gel. In an attempt to produce gels with a suitable polymer concentration, cross-linked agarose derivatives have been prepared with the assumption that cross-linking will improve the stability and sieving efficiency of the gel.

Several different cross-linked agarose derivatives are known in the prior art. U.S. Pat. No. 3,507,851 to Ghetie discloses cross-linking of agarose particles with epichlorhydrin. U.S. Pat. No. 3,959,251 and UK Patent No. 1,352,613 both to Porath et al. disclose stabilization of agarose beads by cross-linking with several bifunctional reagents in the presence of a reducing agent. The resulting beads had greater rigidity, giving higher flow rates when packed into columns for chromatography. The cross-linking reaction was carried out after the gel was formed and the resulting products were in the form of particles.

Cross-linked agarose gels in the form of plates are also known. U.S. Pat. No. 3,860,573 to Honkanen discloses agarose gels cross-linked with a bifunctional reagent containing two equal functional groups selected from acyl chloride, sulfonyl chloride and isothiocyanate. A process for treating polysaccharide gels comprising suspending or dissolving the polysaccharide gel in a solution of 2,4,6-trichloro-1,3,5-triazine, is disclosed in U.S. Pat. No. 3,956,272 to Tixier. However, the cross-linking reactions of Honkanen and Tixier introduced charged groups into the gel-forming polymer.

Honkanen and Tixier reported that their cross-linked agarose gels could be used as media for electrophoresis. Regarding properties of these gel matrices, Honkenen teaches that movement of large molecules (proteins) is more rapid in the cross-linked agarose, which would indicate an increase of effective porosity due to the cross-linking reaction. Tixier discloses that the treated gels had essentially the same characteristics as untreated gels with respect to sieving and resolving power. This result of Tixier is in accordance with the report of Porath (J. Chomatogr. 103 (1975) 49-62) who found that cross-linked agarose beads did not change their porosity.

Gels formed by reacting many different polymers/cross-linker combinations under various cross-linking conditions are described in U.S. Pat. No. 5,541,255 to Kozulic. The cross-linkers react with hydroxyl groups of polymers to form ether linkages without introducing a charged group into the gel. It is possible to use natural or synthetic polymers possessing hydroxyl groups but natural polymers are preferred because of their pronounced hydrophilicity. The most common of such polymers is agarose. Compounds having oxirane or halo groups are particularly suitable as possible cross-linkers. Examples of the cross-linkers include epichlorohidrin, butanediol diglycidylether and 1,2-dibromopropanol. The gel formation and cross-linking reactions proceed simultaneously in a water solution of dissolved agarose. Because of the high ratio of the cross-linker to polysaccharide, the gel is always in the form of a continuous water insoluble bed.

The cross-linked agarose gels described by Kozulic were used to support electrophoresis. The separation range of the gels depended on the polymer type, its concentration, cross-linker type, and cross-linker concentration, as well as the cross-linking conditions. For example, a gel containing 1% of cross-linked agarose gave very good separation of DNA fragments in the size range from about 150 to 3000 bp. Improved resolution of small (200-600 bp) DNA molecules was achieved, as compared to results obtained by using a native agarose polymer. Moreover, the gels formed according to the above invention were soft and elastic and they had improved transparency. However, a main drawback of these cross-linked agarose gels is their impurity. In this regard, the formed gels contain some unreacted cross-linker, byproducts of the gelation reaction, and the base which is used as a catalyst. Accordingly, to produce a gel of well-defined ionic composition, it is necessary to firstly wash the cross-linked gel in water, and then incubate the gel in a desirable electrophoresis buffer. A further draw back arising from the cross-linked gels described by Kozulic is that the gels are not reversible, thus preventing separated components from being recovered.

An alternative way of varying the properties of gels suitable for use in electrophoresis, is to add an additive into a formed gel or into a gelling solution. The additive is chosen such that it improves a particular property of the gel to which it is added. In this regard, additives have been used in combination with agarose gels. As mentioned above, agarose gels have inferior optical properties compared to polyacrylamide gels. This drawback can be partially corrected by adding another polysaccharide into the agarose solution prior to its gelation (U.S. Pat. No. 5,230,832 to Perlman). The sieving properties of agarose gels can be improved by combining them with other gel forming materials such as polyacrylamide (Bode, H. J. (1977) Anal. Biochem. 83, 204-210; Horowitz, P. M. et all. (1984) Anal. Biochem. 143, 333-340). In these gels, the agarose provided mechanical stability, whereas the polyacrylamide served as a sieving medium. Another example includes the addition of polyethylene glycol (PEG) into a pre-formed gel, such as a cellulose acetate gel. In this combination the cellulose acetate served as the stabilizing medium whereas the PEG was the sieving medium (Bode, H. J. (1976) FEBS Letters. 65, 56-58). However, such mixtures have compatibility problems, especially when they contain high percentages of agarose. Moreover, such heterogeneous agarose blends have not afforded a consistent improvement of protein separation patterns. This is particularly so in the context of submerged electrophoresis, where additives not incorporated in the gel structure have a tendency to diffuse out of the gel.

Electrophoresis gels of enhanced selectivity can be produced by adding a preformed polymer (additive) to a polymerization solution containing acrylamide or (N-acryloyl-tris(hydroxymethyl)aminomethane (NAT) and a cross-linker (U.S. Pat. No. 5,840,877 to Kozulic). Agarose, hydroxyethylcellulose and other polysaccharides can be used as preformed polymers. In this connection, it has been noticed that the relationship between the polymers formed by free-radical polymerization in the presence of an additive is complex, since in some instances the newly formed polymer and the preformed additive will become covalently linked by a chain transfer reaction during free-radical polymerization. Moreover, a polymeric additive may be intertwined with the gelled polymers so strongly that for all practical applications it may be considered an integral part of the gel matrix. Alternatively, the additive may be only loosely associated with gel polymers, or it may just remain in the gel interstices, allowing easy diffusion out of the gel. It was found that at a specific ratio of additive to monomer and cross-linker, an enhanced selectivity of the gel was achieved, i.e., the electrophoretic migration of larger molecules was retarded relative to the electrophoretic migration of the smaller molecules. This reduction might be related to the high friction between gel polymers.

Other polysaccharides have been used as additives in polymerization solutions, with the intention of enhancing selectivity of electrophoretic separations. These include dextran, the polysaccharide from locust bean, carubin-type galactomannan (U.S. Pat. No. 5,840,877 to Kozulic; WO 0077059 to Lazar). Such polysaccharides have given rise to a selectivity enhancement, enabling fine resolution on a much shorter gel length than previously possible.

Synthetic polymers have also been added to polymerization solutions of acrylamide or NAT (U.S. Pat. No. 5,840,877 to Kozulic). In this regard, PEG, polyvinyl alcohol and polyvinylpyrrolidone were not able to give gels of enhanced selectivity. However, there was a strong retardation of larger DNA molecules in gels containing linear polyacrylamide.

Graft polymerization involves reacting a monomer with a polymer substrate. Graft polymerization depends on the creation of active sites on the substrate. In free radical-initiated chemical grafting, active sites are usually created as a result of a hydrogen abstraction reaction. The polymerization reaction is thus initiated directly by a polymer chain radical, and when unsaturated monomer is present, polymerization occurs, resulting in the newly formed polymer being covalently bonded or grafted onto the existing polymer molecule.

A number of chemical activators are known. The production of starch graft copolymers or cellulose graft copolymers utilizing polymerization initiators such as hydrogen peroxide, organic peroxides and hydroperoxides have been reported. Yields of grafted chains may be improved by the use of an activator for these initiators such as mild reducing agents, e.g., ferrous ammonium sulfate, sodium sulphoxylate and the like. For the most part, these initiators are nonspecific and induce homopolymerization of single monomers and copolymerization of monomer mixtures, as well as the desired graft polymerization of monomer and monomer mixtures to the substrate. This produces products which tend to separate on storage.

Such problems can be minimized or avoided by the use of a cerium (4+) ammonium salt as an initiator. The cerium ion (4+) interacts with various protonated organic groups, including hydroxyl, carboxyl, amine, etc., to remove an electron to the metal ion, and leave an initiating radical behind on the organic group. In such a system, the metal ion acts as an oxidizer. Thus, the cerium (4+) salt forms a redox pair with an organic reducing agent. For example, U.S. Pat. No. 2,922,768 to Mino et al. teaches the polymerization of vinyl monomers in the presence of cerium salt with organic reducing agents, such as alcohols, aldehydes, thiols, glycols and amines. If a polymeric reducing agent such as a polysaccharide or a poly (vinyl alcohol) is employed, and the oxidation is conducted in the presence of a vinyl or olefin monomer, graft polymerization will occur on the substrate. Although some homopolymerization has been reported using cerium (4+) by Fanta et al. (J. Appl. Polymer Sci., Vol. 10, pp. 919-937, 1966), the most important pathway for cerium (4+) initiation of free radicals as outlined by Fanta (Block and Graft Copolymers, Vol. 1, pp. 1-45, Ed. R. J. Ceresa, John Wiley & Sons, London & New York, 1973) would be expected to give graft copolymers to the exclusion of any homo- or copolymers. Extensive use has been made of this system to graft vinyl monomers to starch, cellulose, dextran, poly(vinyl alcohol) and other polymers possessing hydroxyl groups. The graft copolymerization of vinyl monomers onto cellulose in the presence of cerium salts proceeds readily when the monomer is a polar electron acceptor monomer such as acrylonitrile or acrylates.

The chemistry of polymer-grafting onto polymers containing hydroxyl groups in the presence of cerium (4+) salts has been discussed in the literature (G. Odian, J. Kho. Macromol. Sci. Chem. A4(2) (1970) 317-330). The chain growth radical polymerization is initiated by the abstraction of a hydrogen atom from such a polymer, which is then oxidized to a hydrogen ion via a reversible cerium ion redox reaction (G. Mino and S. Kaizerman. J. Polym. Sci. 31 (1958) 242-243). The activated polymers carry free radicals that rapidly react with vinyl groups of monomers present in solution that initiate polymerization, exclusively on the polymer backbone.

A method of graft polymerization for producing phase supports for partition chromatography is described in U.S. Pat. No. 4,756,834 to Muller et al. The phase support comprises base support particles consisting of an inorganic and/or organic material and an extensive list of such materials is disclosed. A surface layer of polymeric material, preferably polyacrylamide, is attached to the base support particles by graft polymerization. Cerium (IV) ions can be used as the polymerization catalyst. This patent is not concerned with electrophoretic gels. Graft polymerization is also used in U.S.

Pat. Nos. 5,674,946 and 6,291,216 both to Muller to produce activated support materials based on hydroxyl-containing base supports for use in chromatographic separating materials and for immobilization of enzymes. The surfaces of the hydroxyl-containing base supports are covalently bonded to polymers by graft polymerization. The reaction is carried out in the presence of Cerium (IV) ions. Suitable base support listed are agarose-based polysaccharides, cellulose, cellulose derivatives and polymers based on dextran. Acryloylated chlorohydrin-containing alkyl-amines are polymerized onto the base supports in U.S. Pat. No. 5,674,946 and vinyl monomers are polymerized onto the base supports in U.S. Pat No. 6,291,216. These patents are not concerned with the production of a gel for electophoresis.

It has been found recently that monomers such as poly (ethylene glycol)acrylate, poly(propylene glycol)acrylate, glycerol acrylate, hydroxyalkyl acrylate, poly(ethylene glycol)methacrylate, poly(propylene glycol)methacrylate, glycerol methacrylate and /hydroxyalkyl methacrylates may be used to form polymers that are well-suited for use as electrophoresis support media (U.S. Pat. No. 5,290,411 to Zewert and Harrington). In this regard, alkylene glycol esters of methyacrylic or acrylic acid have been polymerized and cross-linked to different degrees to provide electrophoresis support media ranging from viscous liquids to gels. If desired, these monomers may be copolymerized with acrylamide. In general, the resolution with the resulting gels was of the same order as that obtainable with polyacrylamide. Some gels gave sharper banding than polyacrylamide. Moreover, the use of such monomers has the significant advantage in that they are considerably less toxic than acrylamide. However, these gels have a number of disadvantages (when used in an aqueous environment) compared to acrylamide gels. For example, the gels are not as mechanically robust as acrylamide gels (when using an equivalent amount of cross-linker). Furthermore, the rate of protein migration through the gels is significantly slower than that for acrylamide gels.

The present invention addresses the disadvantages associated with the above prior art.

DETAILED DESCRIPTION OF THE INVENTION

Accordingly, in a first aspect, the present invention provides a method of preparing a gel for use in electrophoresis, which method comprises:
(a) providing a mixture comprising a solvent, agarose or a derivative thereof, one or more vinyl monomers, and a polymerisation initiator, the initiator forming a redox system with agarose or the derivative thereof;
(b) exposing the mixture to polymerisation conditions to graft-polymerise the one or more monomers onto the agarose or derivative thereof; and
(c) allowing the mixture to form a gel.

In a second aspect, the present invention provides a kit for preparing a gel for use in electrophoresis, said kit comprising:
(a) agarose or a derivative thereof;
(b) one or more vinyl monomers; and
(c) a polymerisation initiator capable of forming a redox system with agarose.

In a third aspect, the present invention provides a method of making a graft copolymer, which method comprises:
(a) providing:
(i) agarose or a derivative thereof;
(ii) one or more vinyl monomers, wherein the one or more vinyl monomers contain an ethylene glycol moiety or a poly(ethylene glycol) moiety;
(iii) a polymerisation initiator capable of forming a redox system with agarose;
(b) contacting the agarose or derivative thereof with the initiator; and
(c) graft-polymerising the one or more monomers onto the agarose or derivative thereof.

It has surprisingly been found that the electrophoretic gels of the present invention have several advantages when compared to standard agarose gels. In particular, the electrophoretic gels according to the present invention have improved elasticity, higher water-holding capacity, lower tendency to undergo syneresis and improved stability. This is a particular advantage in the field of producing pre-cast electrophoresis gels. The gels of the present invention are also thermoreversible, enabling easy isolation of separated products. Furthermore, the gels according to the present invention are at least as effective as standard agarose gels in separating charged molecules such as nucleic acids.

Preferably, the polymerization initiator used in the present invention comprises cerium (4+). More preferably, the polymerization initiator is cerium (4+) ammonium nitrate.

The monomers used in the present invention are not particularly limited. Preferable monomers are selected from the group consisting of acrylamide, N-vinylpyrrolidone, and esters of acrylic or methacrylic acids with the following: ethylene glycol, propylene glycol, ethylene glycol methyl ether, propylene glycol methyl ether, poly(ethylene glycol), poly(propylene glycol), poly(ethylene glycol)methyl ether and poly(propylene glycol)methyl ether. Preferably, the monomers contain an ethylene glycol or poly(ethylene glycol) group. More preferably, the monomers are poly(ethylene glycol)acrylates, poly(ethylene glycol)methacrylates, poly (ethylene glycol)diacrylates, poly(ethylene glycol) dimethacrylates, poly(ethylene glycol)methyl ether acrylates or poly(ethylene glycol)methyl ether methacrylates. Preferably still, the monomers are poly(ethylene glycol)methyl ether acrylates or poly(ethylene glycol)methyl ether methacrylates. When the monomers comprise poly(ethylene glycol), the poly(ethylene glycol) moiety preferably consists of an ethylene glycol oligomer with a degree of polymerization between 2 and 45, more preferably between 2 and 20, the most preferably between 4 and 8.

In the context of the present invention, the term poly(ethylene glycol) encompasses poly(ethylene glycol) that has been substituted at one or both of the ends comprising the hydroxyl groups.

The polymerization reaction is carried out in an appropriate solvent, preferably water. The concentration of monomer in the polymerization reaction is preferably 2% or less (w/v), and more preferable in the range 0.25 to 1%.

The concentration of initiator in the polymerization reaction is preferably 0.005% or less, and is more preferably in the range 0.0004 to 0.002% (w/v).

The present invention also provides an isolated graft copolymer obtainable by the method of the present invention. The isolated graft copolymer should not contain impurities or contaminants at a concentration which adversely affects the gelation properties thereof. Furthermore, it is preferred that contaminants such as agaropectin and/or residual monomers should be at a concentration of less than 20% (w/v), more preferably less than 10% (w/v), in the agarose or derivative, or in the final product. Preferably, the graft copolymer is isolated such that it has a purity of greater than 80%. More preferably, the graft copolymer has a purity of 90% or greater, and still more preferably, 95% or greater.

According to one aspect of the invention, the agarose or derivative thereof used to prepare the graft copolymer is preferably sufficiently pure and/or of sufficiently high molecular weight to be capable of forming a gel for use in electrophoresis without further isolation, and preferably has a purity of greater than 80%. More preferably, the agarose or derivative thereof has a purity of 90% or greater, and still more preferably, 95% or greater.

The present invention will now be described in more detail, by way of example only, with reference to the following figures.

The gels according to the present invention can be made from a pre-prepared agarose graft copolymer. Alternatively, the gel can be prepared in situ, i.e., the gel can be prepared directly from the polymerization ingredients. In the latter case, the polymerization reaction may be carried out in an electrophoresis chamber i.e., the container in which electrophoresis will be performed. Alternatively, polymerization may be carried our in a container and the polymerisation mixture comprising the graft copolymer can be transferred into a further container e.g., an electrophoresis chamber.

The gels according to the present invention are preferably thermoreversible. Accordingly, pre-formed gels can be heated above the gelling temperature of the gel and subsequently poured into a container of choice (e.g., an electrophoresis container).

The gels can be used in any method that exploits electrophoresis. For example, the gels can be used to separate nucleic acids (such as DNA, RNA, cDNA and nucleic acid analogues), proteins or enzymes.

Agarose or an agarose derivative are used in the present invention. By agarose derivative is meant a derivative that has substantially the same basic structure as agarose (i.e., comprising the basic repetitive unit containing 3,6-anhydro-L-galactose and D-galactose) but wherein the saccharide moieties comprise one or more substituents that differ from that of agarose. The agarose derivative must be suitable for forming electrophoretic gels.

The agarose used for the polymerization is prepared by conventional procedures. Typically, powder agarose is dispersed in a required volume of solvent (preferably water) and placed in a flask. The dispersion is heated (e.g, in a microwave), typically up to the boiling point. After dissolution of the agarose, the solution is typically maintained at a temperature above the gelling temperature (e.g., 50° C.) under nitrogen to remove air.

Graft polymerisation onto agarose is typically carried out in an aqueous solution. The procedure of making the graft copolymer typically involves the addition of monomer into an aqueous solution of agarose (or a derivative thereof) kept above the gelling temperature of the agarose, usually above 40° C., preferably about 50° C., and preferably under nitrogen flow. The initiator (typically, cerium (4+) ammonium nitrate dissolved in diluted nitric acid) is added.

The temperature at which graft-polymerisation of the vinyl monomers is carried out should be controlled and the inside of the reaction vessel is preferably maintained with an inert atmosphere to provide reasonably rapid polymerisation. The graft polymerisation reaction is typically carried out for a period of at least 3 hours, usually for a period in the range of 3 to 5 hours and preferably for a period of about 4 hours.

The vinyl monomers that are used for grafting onto agarose (or a derivative of agarose) include those which are known to be useful in the formation or modification of a gel suitable for electrophoretic separations. Preferred monomers are selected from the group consisting of acrylamide, N-vinylpirrolidone, and esters of acrylic or methacrylic acids with the following: ethylene glycol; propylene glycol, ethylene glycol methyl ether, propylene glycol methyl ether, poly(ethylene glycol), poly(propylene glycol), poly(ethylene glycol)methyl ether and poly(propylene glycol)methyl ether. More preferably, the monomers are poly(ethylene glycol)acrylates, poly(ethylene glycol)methacrylates, poly(ethylene glycol)diacrylates, poly (ethylene glycol)dimethacrylates, poly(ethylene glycol)methyl ether acrylates or poly(ethylene glycol)methyl ether methacrylates. Preferably still, the monomers are poly(ethylene glycol)methyl ether acrylates or poly(ethylene glycol) methyl ether methacrylates. When the monomers comprise poly(ethylene glycol), the poly(ethylene glycol) moiety preferably consists of an ethylene glycol oligomer with a degree of polymerization between 2 and 45, more preferably between 2 and 20, and most preferably between 4 and 8.

More than one monomer can be employed in the polymerization reaction. By more than one monomer is meant two or more different types of monomer. In this embodiment, a copolymer may be grafted onto the agarose or agarose derivative.

The initiator of the present invention is capable of forming a redox system with agarose. Preferably, the initiator is capable of forming a complex with one or more hydroxyl groups of agarose. In this regard, it is preferable that the initiator is capable of forming a complex with one or more hydroxyl groups of agarose, which complex disintegrates under redox reaction.

The initiator typically forms a redox pair with the agarose (or agarose derivative). Thus, the initiator acts as an oxidising agent and the agarose (or agarose derivative) acts as a reducing agent, and a free radical is formed on the agarose. Typically, a free radical will be formed on the carbon atom directly adjacent to an OH group on agarose (or agarose derivative). This carbon may be the C(6) atom of the galactopyranose ring of agarose (leading to graft polymerization onto this carbon atom), but the formation of free radicals at other carbon atoms adjacent to hydroxyl groups may also occur.

Preferably, the initiator comprises a metal ion, and the metal ion acts as an oxidising moiety. Typically, the metal ion is cerium (4+). The initiator is preferably cerium (4+) ammonium nitrate. Without being bound by theory, it is thought that the mechanism of the interaction between cerium (4+) and molecules (or polymers) containing an OH group is as shown below, where a free radical is formed on the carbon atom adjacent to the OH group.

In the above scheme [X] represents a complex of cerium (3+) with a polymer containing an OH group.

Agarose usually constitutes from 0.4 to 2% (w/v) of the graft-polymerization solution, preferably 0.7, 1.0 or 2.0% (w/v). The concentration of monomer in the solution depends on the agarose concentration and monomer type and is preferably not higher than 2% (w/v). The molar ratio of a monomer to each agarose repeat unit is preferably in the range 1:6 to 2:1 and more preferably in the range 1:3 to 1:1. The agarose repeat unit used in the present invention preferably has molecular weight of 306.

For the preferred monomers such as poly(ethylene glycol) methyl ether acrylates and poly(ethylene glycol)methyl ether methacrylates with a degree of polymerization of ethylene glycol residues between 4 and 8, the preferred weight ratio of monomer to agarose is in the range 1:8 to 3:1 and is most preferably in the range 1:4 to 1:1. Thus, the concentration of monomer is typically in the range 0.25 to 1 wt. %. At relatively high concentrations of monomer, the graft-polymerization medium becomes very viscous thus impeding formation of homogeneous gels. Moreover, modified agarose containing a relatively high content of grafted chains exhibits poorer resolving properties in electrophoretic separations.

The concentration of the initiator expressed as a molar ratio of the initiator to the monomer is preferably in the range 1:100 to 1:2000, typically in the range 1:500 to 1:1000 and the most preferably about 1:700. Thus, it is preferable that the concentration of the initiator does not exceed 0.005 wt. % and is typically in the range 0.0004 to 0.002 wt. % (w/v). At relatively high concentration of the initiator no gel is formed because of the collapse of the fine hydrogen bonding responsible for formation of the agarose gel matrix. A concentration of initiator that is too low gives rise to a slow graft-polymerization process.

The method of making the gel according to the present invention preferably comprises (a) providing a mixture comprising a solvent, agarose or a derivative thereof, one or more vinyl monomers, and a polymerisation initiator, the initiator forming a redox system with agarose or the derivative thereof;

(b) exposing the mixture to polymerisation conditions to graft-polymerise the one or more monomers onto the agarose or derivative thereof; and (c) allowing the mixture to form a gel.

In this regard, the preferred concentrations/conditions mentioned above apply equally to those used in making a gel directly from the polymerization mixture as they do to making the graft copolymer itself.

The step of allowing the mixture to form a gel preferably comprises cooling the mixture.

Table 1 summarises the effect of monomer type, agarose concentration, monomer concentration and initiator concentration on the resulting gel properties. Accordingly, an appropriate choice of monomer and concentration of agarose, monomer and initiator may be derived from Table 1. This table summarises the effect of these parameters on gelling temperature, optical density (transparency), strength, elasticity and suitability for electrophoresis of the modified agarose gels. The initiator used in examples 1 to 39 of Table 1 was cerium (4+) ammonium nitrate.

By "modified agarose gels" is meant gels comprising an agarose graft copolymer obtainable from the methods of the present invention.

The kinetics of the graft-polymerization of the monomers onto agarose at 50° C. was studied using spectrophotometric and bromide-bromate methods.

In spectrophotometric methods, aliquots of the reaction mixture were sampled every 30 minutes, and the optical density at 210 nm of the diluted sample solutions was measured. Absorbance at 210 nm is dependent on the double bonds of the monomer and reduces when the concentration of monomer decreases.

In the bromide-bromate study, aliquots of the reaction mixture were sampled every 30 minutes and dissolved in acetic acid. The sample solution was mixed with bromide-bromate solution and a small amount of concentrated HCl, and left for 20 minutes. Aqueous KI solution was added and the solution titrated with standard $Na_2S_2O_3$ solution. The volume of $Na_2S_2O_3$ solution increases when the monomer concentration drops.

The above studies revealed that, at 50° C., the graft-polymerization was over within 3-4 hours. These data indicate that a preferred reaction time for the graft polymerization process is in the range of 3-4 hours. A reaction time of about 4 hours is most preferable.

Agarose forms a gel when a homogeneous boiling solution is cooled to a temperature below the ordering temperature (coil-helix transition), which is typically around 35° C. The gel is formed when an infinite three-dimensional network of agarose fibers, formed by helices of agarose, develops. The melting of agarose gels occurs at a comparatively higher temperature (around 90° C.). In this regard, the gelling and melting temperatures of the modified agarose gels were evaluated.

The gelling temperature was determined using Brookfield viscometer. A hot solution of modified agarose was poured into a 50 ml beaker, and the solution was cooled down at a rate of 1° C. min$^{-1}$ constantly measuring its viscosity. At around the gelling temperature a sharp increase in viscosity of the solution was observed.

The melting temperature was determined by the method of Ubbelohde. A hot solution of modified agarose was poured into a crucible containing a small hole in the bottom and equipped with a thermometer. The gel was allowed to set and the crucible was inserted into a test-tube. The test-tube was heated at the rate of 1° C. min$^{-1}$. The temperature at which the melted gel drops is fixed as the melting temperature.

The gelling temperature of the modified agarose gels was 2-4° C. lower than standard agarose gels (Table 1). This effect was more evident for the gels with a lower concentration of polymer (i.e. lower concentration of vinyl monomer). The melting temperature of the modified agarose gels was also slightly lower (typically by 1-3° C.) compared to standard agarose gels of the same concentration.

Moreover, the modified agarose gels according to the present invention melted more easily than standard agarose gels and, in contrast to standard agarose gels, they melted with less foaming. Indeed, the gels melted without any substantial foaming. Despite the lower gelling temperature, the modified agarose gels also set to a stable form at a faster rate than standard agarose gels. These findings illustrate that the gels according to the present invention have improved handling properties when compared to standard agarose gels.

The transparency of the modified agarose gels was determined using spectrophotometric methods. Absorbance measurements of 1 cm thick gels, prepared by cooling agarose or modified agarose solutions in cuvettes, were taken at 600 nm. After preparation, the cuvettes with the gels were allowed to set for 24 h in the fridge (5° C.).

Optical densities of standard agarose gels of 0.7; 1.0 and 2.0% concentration are respectively 0.17; 0.18 and 0.25. Gels prepared using agarose (0.7 wt % in solution) with PEGMEA, PEGMEMA, VP or PEGDA monomers had, in most cases, increased optical densities [up to 0.20-0.23 (Table 1)]. Any reduction in transparency of the modified agarose gels was negligible.

Three commonly employed methods for measuring mechanical properties of the gels are available. The first method, known as the Bloom test, measures deflection. It determines the force necessary for a probe (usually 13 mm in diameter) to deflect the surface of the gel four millimeters without breaking the gel. The result is expressed in Bloom grams or "Bloom" and usually varies between 30 and 300 grams. This method is most often used on soft gels. The second method uses a larger diameter probe (usually an inch) and penetrates the gel far enough to rupture it. The force needed to rupture the gel and the distance at which it ruptures are important. This test is usually used for stiffer gels such as ones made from pectins and agar. The third test is used for very stiff gels. A cylinder of the gel is placed between two plates and the force necessary to rupture the gel is measured as the plates come together.

In order to compare the compression of the gels according to the present invention ('modified gels'), the second of these methods was employed. A self-made appliance based on an old double-pan balance was used. Test gels (15 mm thick) were prepared in 100 ml beakers. After preparation, the gels were allowed to set for 24 h in the fridge (5° C.). The beaker with the gel was placed on the sample pan and an empty 2000 ml beaker placed on the weight pan. Using sliding weights and/or free weights, the two sides were balanced evenly. The punch rod with a conical end (10 mm in diameter) was suspended over the sample pan of the balance while a large burette with water was placed over the 2000 ml beaker on the weight pan. The punching rod was lowered until it just touched the surface of the sample gel. Then the stopcock on the burette was opened enabling the water to pour into the 2000 ml beaker until the sample gel was broken. The stopcock was then closed and the amount of water missing was noted. The flow rate of water from the burette was 15 ml/s. The amount of water poured into the 2000 ml beaker was equated to the weight compressing the gel. The data obtained in the compression tests were expressed in g/cm².

The elasticity of the modified agarose gels was tested using a method similar to the Bloom test. Again, a self-made appliance based on an old double-pan balance was used. For elasticity test specimens (100 mm×10 mm×13 mm), hot agarose solutions were poured between two 10 mm height plastic plates separated by 13 mm thick spacer, cooled to ambient temperature and left for 24 h at 5° C. A gel specimen (10 mm in height) was placed on a ring-type holder with a 55 mm hole in the middle, and the holder was put on the sample pan. An empty 200 ml beaker was placed on the weight pan and the two sides were balanced evenly using the sliding weights and/or free weights. The metal rod with a spherical end (13 mm in diameter) was suspended over the sample pan of the balance while the burette with water was over the 200 ml beaker on the weight pan. The punching rod was lowered until it just touched the surface of the sample gel. Then the stopcock on the burette was opened enabling the water to pour into the 200 ml beaker until the metal rod deflected the surface of the gel by 10 millimeters.

At this time, the stopcock was closed and the amount of water missing was noted. The flow rate of water from the burette was 15 ml/s. The amount of water poured into the 200 ml beaker was equated to the weight deflecting the gel specimen for 10 mm. The data of elasticity tests were expressed in grams.

The results of the compression and elasticity tests are shown in Table 1.

Table 1 shows that modification of agarose according to the present invention does not significantly change the strength of the gels. The value of the relative strength of the gels, which is expressed as the ratio of the strength of a modified agarose gel to the strength of a standard agarose gel, does not deviate significantly from one. The strength of the gels is dependent on the concentration of agarose but is not dependent on the type or concentration of monomer.

The elasticity of the modified agarose gels according to the present invention is significantly higher than the elasticity of the gels formed by standard agarose (for a given concentration of agarose). The higher the elasticity of a gel the smaller the weight needed to deflect the gel specimen by 10 mm. According to the relative elasticity value, which is expressed as the ratio of the weight needed to deflect a standard agarose gel to the weight need to deflect a modified agarose gel, modification of agarose (in 0.7% solution) with PEGMEA increased the elasticity of the resulting gels by 1.3-1.5 times. Modification of agarose with VP was even more effective.

The elasticity and flexibility of the modified agarose gels according to the present invention enables them to be easily handled, a property which is very important if electrophoretic gels are to be produced in precast form.

The loss of liquid from an electrophoretic gel with time (referred to as syneresis) is undesireable. This is particularly so in the context of electrophoretic gels which are stored for long periods before use. During syneresis, liquid in the gel oozes out of the gel and the gel changes concentration, shape, form and separation characteristics. As a result, the bands of separated material (e.g., DNA) that are formed during electrophoresis are bent or even converge with one another. Although agarose electrophoretic gels are relatively stable, any improvement related to inhibition of syneresis would be a substantial advantage, particularly in the field of precast gels.

Figure 5:
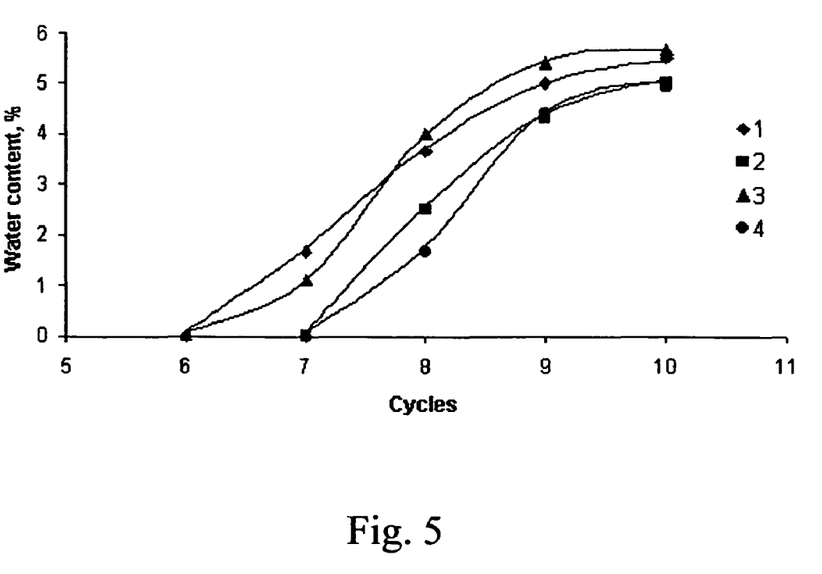
FIG. 5 shows the content of exuded water from standard and modified agarose gels as a function of freeze-thaw cycles. Lines 1 and 3 represent standard agarose gels and lines 2 and 4 represent modified gels with PEGMEA (1%). The agarose concentration was 0.7% (lines 1 and 2) and 2.0% (lines 3 and 4), and the gel media TAE buffer (lines 1 and 2) or water (lines 3 and 4).

The susceptibility of a gel to suffer from syneresis can be evaluated by determining the freeze-thaw stability of a gel. The freeze-thaw stabilities of agarose gels and gels comprising agarose graft copolymers employed in the present invention have been studied by freezing agarose gels and modified gels at −18° C. for 24 h, thawing them at boiling temperature, and then allowing them to cool again so as to re-form a gel. The volume of the exuded liquid phase was measured. This freeze-thaw stability was determined for ten cycles. The results are shown in FIG. 5.

When standard and modified agarose gels were frozen and thawed for six cycles, no separation of water was detected in any cycle i.e., the percentage of syneresis was zero. This shows that both types of agarose gels have a low susceptibility to syneresis. A small amount of water was exuded after 7 cycles from standard agarose gels and after 8 cycles from modified agarose gels. After 9 and 10 freeze-thaw cycles the percentage of water separation increased slowly but in every case the content of exuded water was lower for the modified agarose gels. This shows that the modified agarose gels comprising the agarose graft copolymers according to the present invention have a reduced tendency to undergo syneresis than standard agarose gels.

Syneresis is related to the formation of a more compact form of an interpenetrated network in the gel. These changes depend on the structure of the gel-forming polymer and are a time-dependent relaxation phenomenon. Without being bound by theory, it is thought that modification of the agarose structure by grafting thereto monomers according to the present invention, particularly bulky, branched polymers, such as PEG acrylates, helps to prevent these changes from occurring, thereby helping to provide a structure which is more resistant to syneresis.

The gel compositions of the present invention have high water-holding capacities and are stable against desiccation. In this regard, when kept at room temperature in open beakers, the time taken for the modified agarose gels according to the present invention to dry up and form films of constant weight was approximately 1.5 times longer than the time taken for standard agarose gels of the same concentration. Poly(ethylene glycol) grafts are excellent water holders, and so monomers comprising poly(ethylene glycol) groups are particularly preferred in the present invention.

The improved water-holding properties (e.g, resistance to syneresis and stability against desiccation) of the gels according to the present invention are achieved without detracting from the other important characteristics of the gel composition, e.g. strength, porosity and efficiency of separation.

The gels according to the present invention can be run in various formats known in the art. For example, the gels can be run in submerged gel electrophoresis mode.

The gels can be run at different electric field strengths. Typically, the gels are electrophoresed at 20 V/cm for approximately 1 hour in order to allow easy comparison of different gels.

The gel length can be varied to satisfy the requirements of specific separation needs. The gels can be run in different buffer solutions. TAE buffer solution containing 40 mM TRIS-acetate and 1 mM EDTA may be used when running the gels of the present invention in submerged gel electrophoresis mode. TBE buffer solution containing 90 mM TRIS-borate and 2 mM EDTA is preferably used for a high-voltage long-lasting electrophoresis, as it has greater buffering capacity. TBE buffer is preferred also in minigel and midigel boxes containing typically small buffer reservoirs which tend to exhaust buffers more readily than larger gel boxes. 0.1 M Na-borate buffer containing 2 mM EDTA may be used successfully with the gels of the present invention.

As mentioned above, the polymerization initiator used in the present invention is an oxidizing agent. In a preferred aspect of the present invention, cerium (4+) ammonium nitrate is used as a graft-polymerization initiator. Cerium (4+) ammonium nitrate is a strong oxidizer. Those skilled in the art know that cerium (4+) ions (or other strong oxidizers) may oxidize some functional groups (e.g., epoxy) of agarose during graft-polymerization. Moreover, some of the initiator may be left after the graft-polymerization reaction, thereby maintaining oxidizing conditions during storage of the gels of the present invention. Furthermore, some monomer (e.g., several percents) may be left unpolymerized. These undesirable factors may be avoided by adding a reducing agent (typically 5-10 mM) of dithiothreitol, optionally together with the buffer stock solution, to the (preferably heated) solution of modified agarose just at the end of the modification (polymerization) reaction. The reducing agent typically generates and maintains a reducing environment in the gel during storage. A particularly preferred reducing agent is dithiothreitol. In this regard, the present inventors have found that dithiothreitol can be used as a component of the electrophoresis buffer without any visible effect on the separation quality.

The present inventors have found that the separation range of the gels of the present invention depends on the electrophoretic conditions, primarily electric field strength and running time. For example, agarose (0.7%) modified with PEG-MEA (0.25%) gave good separation of DNA fragments in the size range from about 100 to 20000 bp, when electrophoresis was carried out for 1 h at 20 V/cm. A 2.0% agarose gel modified with 1.0% of PEGMEA and run at the same conditions gave good resolution in the size range from about 50 to 3000 bp. These and other data teach that the separation range of the gels of the present invention is slightly better than that of standard agarose gels. Furthermore, electrophoretic mobility in most of the modified agarose gels was slightly higher than that found in standard agarose gels. In conclusion, the electrophoretic behavior of the gels of the present invention is either similar or better than that found for gels prepared using standard agarose.

The efficiency of separation of nucleic acid fragments run through the gels of the present invention, and the sharpness of the bands, depends on the type of monomer used to for the graft copolymer, its concentration and the concentration of initiator. A qualitative comparison of the efficiency of the electrophoretic separation of the gels of the present invention, as compared to standard agarose gels, is presented in the Table 1. The results of electrophoresis were rated qualitatively by rating the gels on the following scale: excellent—fine separation of DNA fragments which is equal or superior to that in a standard agarose gel of the same concentration; good—fine separation of DNA fragments which is equal or somewhat inferior to that in a standard agarose gel of the same concentration; fair—moderate separation of DNA fragments but which is worse than that in a standard agarose gel due to loss of sharpness of bands and/or interflow of same bands; poor—unsatisfactory separation of DNA fragments and which is worse than that found in a standard agarose gel.

Referring to Table 1, run No.s 1 to 7 and 10 illustrate how the choice of modifying monomer affects electrophoresis in the gels of the present invention. The best results were found with poly(ethylene glycol)methyl ether acrylate and methacrylate, each with a degree of polymerization in the poly(ethylene glycol) residue of about 8 (run No. 6 and No. 10). The least best results were found for poly(ethylene glycol) acrylate (run No. 3) and poly(ethylene glycol)methyl ether methacrylate with a relatively high degree of polymerization in the poly(ethylene glycol) residue (about 44, run No. 7). In PEGMEMA3-modified agarose gel (run No. 7), the sorption of ethidium bromide was evident and the ground-colour was strong. High sorption of the dye is related possibly to a supramolecular structure comprising relatively long poly(ethylene glycol) residues in the graft-copolymer forming the gel. In some PEGA-modified agarose gels (for example, run No. 3), some bands were poorly resolved, and the separation range was contracted. These drawbacks may be explained by extra cross-linking between poly(ethylene glycol)acrylate macromolecules due to the reaction between the terminal OH group of the poly(ethylene glycol) residue and cerium (4+). Extra cross-linking is also expected in PEGDA-modified agarose gels because of the presence of two double bonds in the monomer molecule. However, PEGDA-modified agarose gels gave relatively better electrophoretic results (run No.s 4 and 31-33), especially at low monomer concentrations (run No. 33). The use of 1-vinyl-2-pyrrolidinone as the modifying monomer also yielded gels with improved electrophoretic properties (run No.s 2 and 35), especially at lower monomer concentrations (run No. 35).

Run No.s 10 to 13 highlight the effect of initiator concentration on the results of electrophoresis while runs No.s 13 to 16 highlight the effect of monomer concentration. Monomer concentration doesn't have any remarkable effect on the results of electrophoresis. The most favorable concentration of the initiator depends on concentration of a monomer.

Run No.s 17 to 20 and run No. 10 refer to gels of different agarose concentration at a fixed ratio of modifying monomer to agarose. The gel with the lowest concentration (run No. 17) was difficult to handle, and some DNA bands were diffused to a greater extent relative to gels employing a higher agarose concentration. The gel with the highest concentration (run No. 20) gave fair results. This is not unexpected bearing in mind that under modification of 2.0% agarose solution with 3.0% of PEGMEA, a very viscous, unmixable mass resulted after 1 h of reaction time. Modification of 2.0% agarose solution with a lower concentration of monomer (run No.s 21 to 23) proceeded without complications and gave excellent electrophoresis results.

Comparison of run No.s 8 to 10 shows that the optimal temperature for the polymerization according to the present invention is 50° C. Run No.s 24 and 25 evidently show that low-molecular-weight agarose (TopVision™ LM GQ agarose) is not suitable for production of electrophoretic gels of the present invention. Run No.s 35 to 37 show that a low monomer concentration could be favorable in many cases. In this regard, employing a low concentration of the monomer PEGMEA gave excellent separation of multimeric plasmid DNA forms. Run No.s 38 and 39 illustrate the suitability of using TBE and Na-borate buffers (rather than the TAE buffer used in the other runs).

The above results clearly demonstrate that gels according to the present invention perform electrophoresis at least as well as standard agarose gels. Moreover, the gels of the present invention have been shown to have a higher elasticity, a higher water-holding capacity, a lower tendency to suffer from syneresis, and an improved stability of the gel matrix. These properties make them particularly suitable for use as pre-cast gels.

EXAMPLES

Example 1

Graft-polymerization of Poly(ethylene glycol)methyl Ether Acrylate (PEGMEA, $M_n$ 454) onto Agarose.

Powder agarose (2.45 g) is dispersed in 350 ml of deionized water in a 500 ml three-neck round-bottom flask. The dispersion is heated in a microwave oven up to boiling sometimes mixing it for better homogenization. After full dissolution of agarose, the flask was connected to a reflux condenser, and the solution is tempered to 50° C. and is held at that temperature under nitrogen flow for 20 min. to oust the air. Than under magnetic stirring 3.21 ml (3.5 g) of PEGMEA was gently added into the flask. Finally the solution of 0.0064 g of cerium (4+) ammonium nitrate in 3.5 ml of 0.01 N aqueous nitric acid was dropped. The flow of gaseous nitrogen was maintained during the reaction of graft-polymerization to ensure inert atmosphere in the flask. The solution in the flask was stirred at 50° C. for 4 hours. The resulting viscous modified agarose solution was poured into the beaker and let to cool down forming a gel.

Example 2

Kinetics of Graft-Polymerization of Pegmea ($M_N$ 454) onto Agarose.

A. Spectrophotometric method.

Graft-polymerization of PEGMEA onto agarose was carried out by the method disclosed in the example 1. 2.5 ml aliquots of the reaction mixture were sampled every 30 min. and diluted to 50 ml using bidistilled water. Optical density of the solution at 210 nm in 1 cm thick quartz spectrophotometer cell was measured using spectrophotometer SF-26. The residual amount of PEGMEA in the sample solution compared to the initial value (%) was calculated as the ratio:

$$X = \frac{D}{D_0} \times 100,$$

where D—optical density of the reaction mixture after fixed time of grafting;
$D_0$—optical density of the reaction mixture before grafting.

B. Bromide-bromate method.

Graft-polymerization of PEGMEA onto agarose was carried out by the method disclosed in the example 1. 2 g aliquots of the reaction mixture were sampled every 30 min., dissolved in 6-8 ml of 50% acetic acid and diluted to 10 ml. 25 ml of 0.1 N bromide-bromate solution, 10 ml of the sample solution and 5 ml of concentrated hydrochloric acid were poured into a conical flask, mixed carefully and left for 20 min. Than 5 ml of 10% aqueous KI solution was added and the content of the flask was titrated with 0.01 N $Na_2S_2O_3$ using several drops of 1% aqueous starch solution as indicator. Monomer concentration in the sample C (%) was calculated as follows:

$$C = \frac{(V_1 - V_2) \times N \times M \times 100}{g \times 2 \times 1000},$$

where: $V_1$—volume of $Na_2S_2O_3$ solution used for titration of blank solution, ml;
$V_2$—volume of $Na_2S_2O_3$ solution used for titration of sample solution, ml;
N—normality of $Na_2S_2O_3$ solution (0.01);
M—molecular weight of the monomer (454);
g—weight of the sample, g.

The residual amount of PEGMEA in the sample solution compared to the initial value (%) was calculated as the ratio:

$$X = \frac{C}{C_0} \times 100,$$

where $C_0$—monomer concentration in the reaction mixture before grafting.

Figure 1:
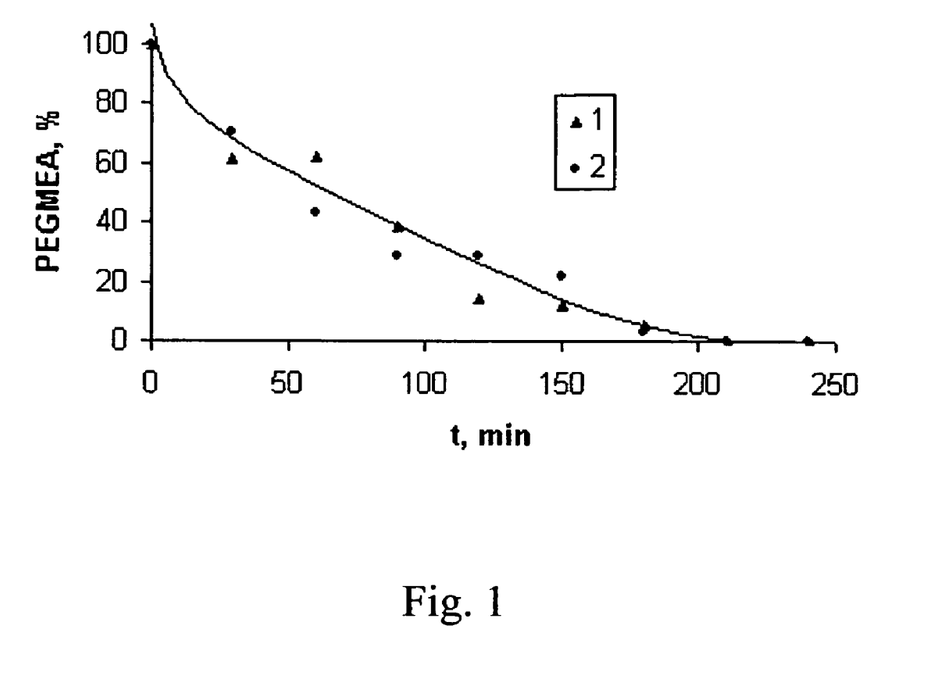
FIG. 1 shows the change in PEGMA concentration during a polymerization reaction according to the present invention. The concentration of PEGMEA is expressed as a % of the initial value (%) in the reaction mixture during graft polymerization onto agarose. The concentration of agarose is 0.7%, the concentration of PEGMEA is 1.0%, the concentration of Ce 4+ is 0.0018% and T=50° C. Triangles (1) represent the results obtained using the spectrophotometric method and circles (2) represent the results obtained using the bromide-bromate method.

The kinetic curve of disappearance of the monomer is presented in the FIG. 1. FIG. 1 shows the residual amount of PEGMEA as compared to the initial value (%) in the reaction mixture during graft polymerization onto agarose. The concentration of agarose is 0.7%, the concentration of PEGMEA is 1.0%, the concentration of Ce 4+ is 0.0018% and T=50° C. Triangles (1) represent the results obtained using the spectrophotometric method and circles (2) represent the results obtained using the bromide-bromate method.

The dispersion of experimental data is significant due to low initial concentration of the monomer (bromide-bromate method) or to alteration in transmittance of the solution caused by physical fluctuation of the grafted chains. Despite large dispersion of the experimental data, both spectrophotometric and bromide-bromate methods give the same curve of disappearance of the monomer during graft-polymerization. One can conclude from the course of the curve that in graft-polymerization at 50° C. the monomer PEGMEA is consumed approximately in 3.5 hours.

Example 3

Preparation of an Electrophoresis Gel 100 g of a modified agarose gel was placed into a beaker and heated in a microwave oven up to melting and boiled for several min. until full homogenization of the modified agarose solution. TAE buffer stock solution (×50) was prepared, per liter: TRIS base 242 g, glacial acetic acid 57.1 ml, 0.5 M EDTA (pH 8.0) 100 ml and water to 1 liter. 2 ml of TAE buffer concentrate and 50 µg of ethidium bromide were added under vigorous stirring to the modified agarose solution and the solution was cast into the cassette for electrophoresis to make electrophoretic media of the dimensions 16×8×0.5 cm. Electrophoresis gel was formed under natural cooling of the cast solution for 1 hour.

Example 4

Dna Electrophoresis using a the Gel Comprising Graft Copolymer.

The gel prepared according to run No. 14 in Table 1 was placed in a standard electrophoretic apparatus for submerged gel electrophoresis. The gel was run at 20° C. in 40 mM Tris-acetate buffer, containing 1 mM EDTA and 0.5 µg/ml ethidium bromide at 20 V/cm of gel length for 1 hour. DNA bands were visualized under UV light. Eight different DNA standard mixtures (commercial markers from MBI Fermentas) were applied to the gel as follows:

Lanes 1,2—O RangeRuler 500 bp DNA Ladder, ready-to-use #SM0643 (0.5 and 0.25 µg);
Lanes 3,4—MassRuler DNA Ladder, Mix ready-to-use #SM0403 (10 and 5 µL);
Lanes 5,6—Lambda DNA/EcoRI #SM0281 (0.5 and 0.25 µg);
Lanes 7,8—Lambda DNA/EcoRI+HindIII #SM0191 (0.5 and 0.25 µg);
Lanes 9,10—Lambda DNA/HindIII #SM0101 (0.5 and 0.25 µg);
Lanes 11,12—Lambda DNA/Eco47 I #SM1051 (0.5 and 0.25 µg);
13,14—Lambda DNA/Eco91 I #SM0111 (0.5 and 0.25 µg);
15,16—MassRuler DNA Ladder, High Range ready-to-use #SM0393 (10 and 5 µL).

Figure 2:
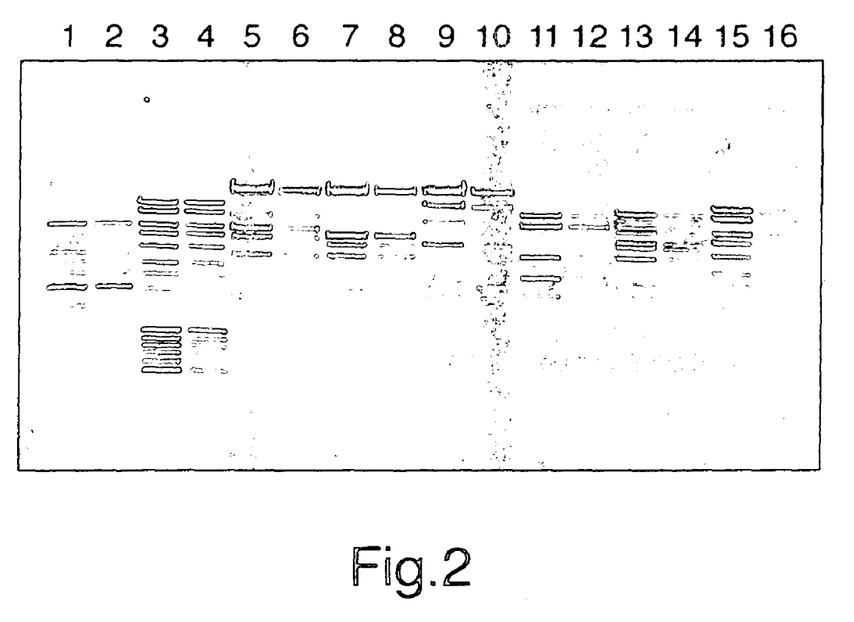
FIG. 2 shows the separation of DNA using an electrophoresis gel according to the present invention.

The results are presented in FIG. 2. At least 19 bands of the MassRuler DNA Ladder Mix ranging from 100 bp to 10000 bp were well distinguishable. At least 12 fragments from 500 bp to 6000 bp at 500 bp increments of the O'Range Ruler 500 bp DNA Ladder were resolved well. The fragments 1371 bp and 1264 bp of Lambda/HindIII mixture migrated in expected order and were separated well. The 2027, 2322 and 4361 bp DNA fragments of the Lambda/HindIII mixture migrated in expected order and were resolved well.

Figure 3:
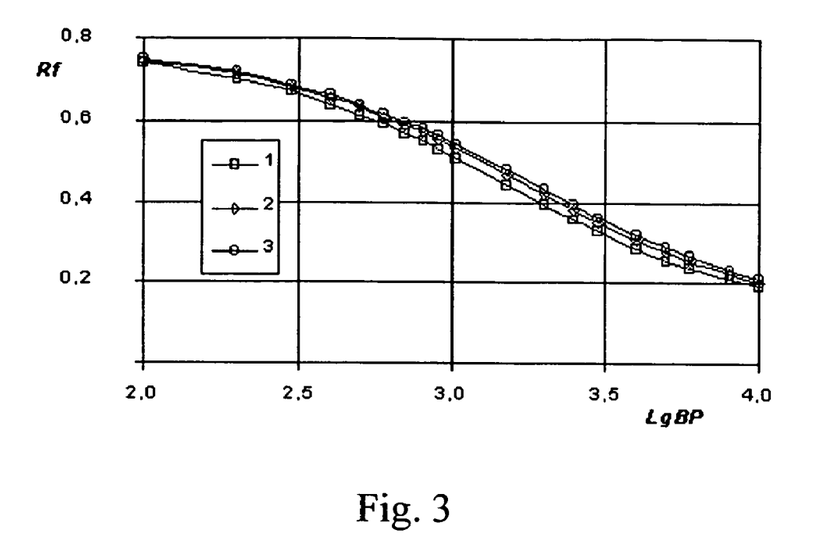
FIG. 3 shows the elctrophoretic mobility of DNA patterns in a standard agarose gel and modified agarose gels according to the present invention. Line 1 represents standard agarose gel formed from run No. 42 of Table 1, line 2 represents the modified agarose gel formed from run No. 14 of Table 1, and line 3 represents the modified agarose gel formed from run No. 10 of Table 1.

For comparative analysis, one quarter of each standard agarose gel and modified agarose gels prepared according to run No.s 14, 15 and 10 were placed in a standard electrophoretic apparatus for submerged gel electrophoresis. DNA standard commercial mixture MassRuler DNA Ladder, Mix ready-to-use #SM0403 from MBI Fermentas was applied to the gels (10 and 5 µL), and the gels were run as described above. Calculation of gel densitograms and their evaluation was performed using software TotalLab™. $R_f$ was calculated by comparing the distance moved by particular bands relative to the distance from the start point to the end of the gel. The electrophoretic mobility of DNA patterns in a standard agarose gel and in some modified agarose gels is presented in FIG. 3. In this FIG. 3, line 1 represents standard agarose gel formed from run No. 42 of Table 1, line 2 represents the modified agarose gel formed from run No. 14 of Table 1, and line 3 represents the modified agarose gel formed from run No. 10 of Table 1. Comparative analysis evidently shows that the electrophoretic mobility of DNA patterns and the fractionation range produced with gels according to the present invention are to very similar to those produced from standard agarose gels.

Example 5

Plasmid Dna Electrophoresis in a Gel According to the Present Invention.

Figure 4:
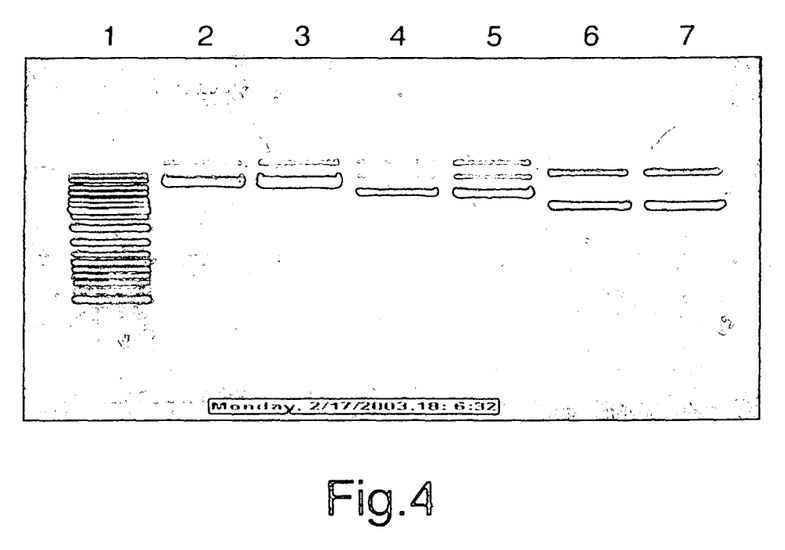
FIG. 4 shows the separation of multimeric plasmid DNA using a modified agarose gel according to the present invention.

Electrophoresis was performed using a modified agarose gel prepared according to run No. 37 (see Table 1) in 1X TBE buffer (90 mM Tris, 90 mM boric acid, 2 mM EDTA) at a constant voltage (5V/cm) at room temperature. Plasmid DNA forms were stained after electrophoresis with 0.5 µg/ml etidium bromide for 20 min and destained with water for 20 min. The gel was documented with Electronic UV Transilluminator Ultralum. The results are shown in FIG. 4. Each lane represents the following: Lane 1—Fermentas' GeneRuler DNA Ladder Mix; lane 2—0.5 µg of plasmid pBMP-4; lane 3—1 µg of pBMP-4; lane 4—0.25 µg of plasmid pUC GK-4; lane 5—0.5 µg of plasmid pUC GK-4; lane 6—0.25 µg of plasmid pUC 300 J; lane 7—0.5 µg of plasmid pUC 300 J.

Example 6

Syneresis of the Gels 30 g of agarose or a gel according to the present invention (a modified agarose gel) was heated in a microwave oven up to melting and full homogenization. The melted agarose solution was poured into 100 ml beaker and let to cool down forming a gel. The beaker was placed into a freezer and refrigerated at −18° C. for 24 h. The frozen gel was thawed and melted in a microwave oven and than left to cool down to room temperature forming a gel again. If the liquid phase was exuded it was separated and weighed. Ten freeze-thaw cycles were repeated for several standard and modified agarose gels of different concentration.

The curves of exudation of water from standard and modified agarose gels reflecting syneresis are presented in the FIG. 5. In FIG. 5, lines 1 and 3 represent standard agarose gels and lines 2 and 4 represent modified gels with PEGMEA (1%). The agarose concentration was 0.7% (lines 1 and 2) and 2.0% (lines 3 and 4), and the gel media TAE buffer (lines 1 and 2) or water (lines 3 and 4).

No free exuded water was fixed even after 6 freeze-thaw cycles for all tested gels. A small amount of water was exuded after 7 cycles from standard agarose gels and after 8 cycles from modified agarose gels. The curves presented in the FIG. 5 illustrate that exudation of water from modified agarose gels starts later and reach a lower value after 9 and 10 freeze-thaw cycles. Although the difference in water exudation from standard and modified agarose gels is not large, it proves that the modified agarose gels have a lower tendency to undergo syneresis.

Example 7

Drying-out of the Gels.

10 g of agarose or a gel according to the present invention (modified agarose) is heated in a microwave oven up to melting and full homogenization. The melted agarose solution was poured into 50 ml beaker and let to cool down forming a gel. The surface of the gel was 18 cm². The gel was left at room temperature (20° C.) and weighed in 24 hours up to constant weight.

Figure 6:
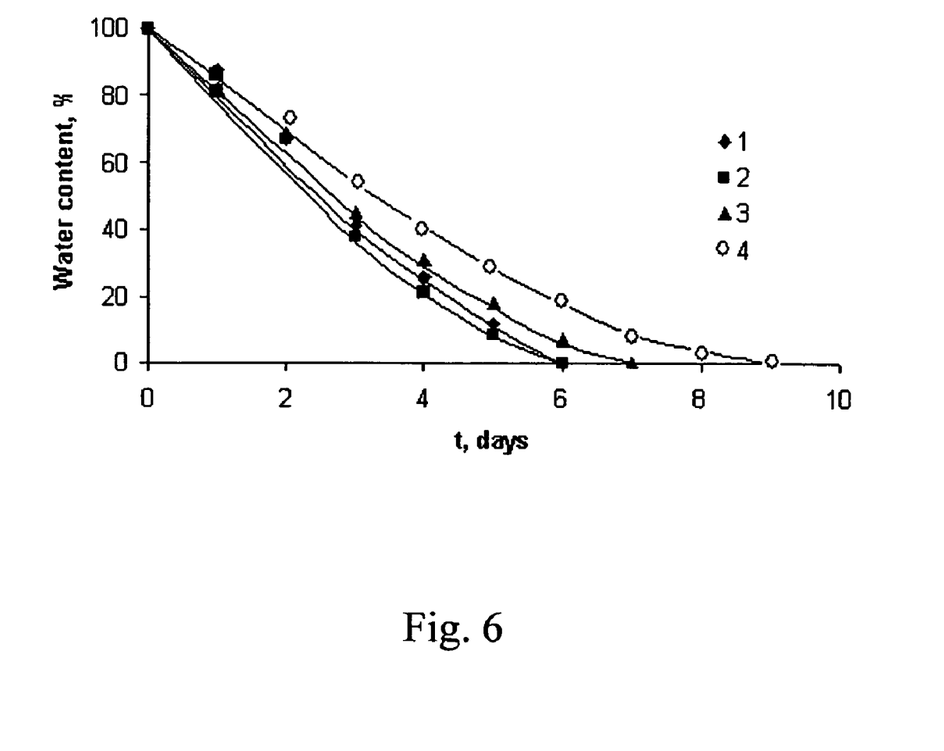
FIG. 6 shows the water content of gels with drying time for standard agarose gels and gels according to the present invention. Lines 1 and 2 represent standard agarose gels (0.7%), and lines 3 and 4 represent modified agarose gels (agarose 0.7%, PEGMEA 1%). The gel media is TAE buffer (lines 1 and 4) or water (lines 2 and 3).

The course of drying of standard and modified agarose gels is presented in the FIG. 6. In FIG. 6, lines 1 and 2 represent standard agarose gels (0.7%), and lines 3 and 4 represent modified agarose gels (agarose 0.7%, PEGMEA 1%). The gel media is TAE buffer (lines 1 and 4) or water (lines 2 and 3).

It is evident standard agarose gel dried most quickly, regardless of gel media. The standard agarose gels dried out forming agarose films in 6 days. The modified agarose gels dried more slowly. The modified agarose gel prepared in TAE buffer dried out in 9 days.

TABLE 1

Some properties of standard and modified agarose gels

| No | Agarose conc., % | Monomer* | Monom. conc., % | Initiator conc., % | Gelling temp. ° C. | Melting temp. ° C. | OD**, 600 nm | Strength, g/cm²//rel.# | Elasticity, g//rel.## | Electrophoresis |
|---|---|---|---|---|---|---|---|---|---|---|
| 1/IV | 0.7 | AA | 1.0 | 0.0018 | | | | | | fair |
| 2/43 | 0.7 | VP | 1.0 | 0.0018 | | | 0.22 | | 34//1.44 | good |
| 3/I | 0.7 | PEGA | 1.0 | 0.0018 | | | | | | poor |
| 4/27 | 0.7 | PEGDA | 1.0 | 0.0018 | | | | | | fair |
| 5/44 | 0.7 | PEGMEMA1 | 1.0 | 0.0018 | | | 0.22 | | 40//1.23 | good |
| 6/45 | 0.7 | PEGMEMA2 | 1.0 | 0.0018 | | | 0.21 | | 42//1.16 | excellent |
| 7/VII | 0.7 | PEGMEMA3 | 1.0 | 0.0018 | | | | | | poor |
| 8/41[x] | 0.7 | PEGMEA | 1.0 | 0.0018 | | | | | 35//1.40 | good |
| 9/40[xx] | 0.7 | PEGMEA | 1.0 | 0.0018 | | | | | 24//1.44 | excellent |
| 10/30 | 0.7 | PEGMEA | 1.0 | 0.0018 | 32 | 90 | 0.23 | 1140//1.02 | 36//1.36 | excellent |
| 11/38 | 0.7 | PEGMEA | 1.0 | 0.00045 | | | 0.20 | | 42//1.16 | good |
| 12/37 | 0.7 | PEGMEA | 1.0 | 0.0009 | | | 0.19 | | 38//1.29 | good |
| 13/36 | 0.7 | PEGMEA | 1.0 | 0.0036 | | | 0.24 | | 33//1.49 | excellent |
| 14/28 | 0.7 | PEGMEA | 0.25 | 0.00045 | | | 0.36 | | 32//1.53 | excellent |
| 15/29 | 0.7 | PEGMEA | 0.5 | 0.0009 | | | 0.17 | | 34//1.44 | excellent |
| 16/31 | 0.7 | PEGMEA | 2.0 | 0.0036 | | | 0.25 | | 38//1.29 | excellent |
| 17/14 | 0.3 | PEGMEA | 0.45 | 0.0008 | 30 | 89 | 0.09 | 286//0.85 | | fair |
| 18/13 | 0.5 | PEGMEA | 0.75 | 0.0013 | 30 | 89 | 0.18 | 755//1.03 | | good |
| 19/15 | 1.0 | PEGMEA | 1.5 | 0.0026 | 34 | 90 | 0.29 | 1480//0.97 | | excellent |
| 20/16 | 2.0 | PEGMEA | 3.0 | 0.0052 | 36 | 91 | 0.47 | 2735//0.90 | | fair |
| 21/18 | 2.0 | PEGMEA | 1.5 | 0.0026 | 38 | 93 | 0.31 | 2960//0.98 | | excellent |
| 22/48 | 2.0 | PEGMEA | 1.0 | 0.0018 | | | | | | excellent |
| 23/19 | 2.0 | PEGMEA | 0.75 | 0.0013 | 38 | 93 | 0.30 | 2990//0.99 | | excellent |
| 24/42 | 2.0[xxx] | PEGMEA | 0.5 | 0.0009 | | | | | 26//3.2 | poor |
| 25/39 | 2.0[xxx] | PEGMEA | 2.0 | 0.0036 | | | | | 28//3.0 | poor |
| 26/46 | 0.5 | PEGMEA | 0.25 | 0.00045 | | | | | 21//1.19 | excellent |
| 27/47 | 0.5 | PEGMEA | 1.0 | 0.0018 | | | | | 23//1.09 | good |
| 28/23 | 0.3 | PEGA | 0.35 | 0.0008 | 29 | | 0.11 | 326//0.96 | | fair |
| 29/21 | 0.5 | PEGA | 0.6 | 0.0013 | 31 | | 0.14 | 765//1.04 | | poor |
| 30/32 | 0.7 | PEGA | 0.25 | 0.00045 | | | | | | fair |
| 31/26 | 0.3 | PEGDA | 0.25 | 0.0008 | 28 | | 0.11 | 345//1.03 | | poor |
| 32/27 | 0.5 | PEGDA | 0.45 | 0.0013 | 31 | 92 | 0.23 | 735//1.00 | | fair |
| 33/33 | 0.7 | PEGDA | 0.25 | 0.00045 | | | 0.17 | | 34//1.44 | excellent |
| 34/34 | 0.7 | AA | 0.25 | 0.00045 | | | | | | good |
| 35/35 | 0.7 | VP | 0.25 | 0.00045 | | | 0.18 | | 25//1.96 | excellent |
| 36/50 | 0.7 | PEGMEMA2 | 0.25 | 0.00045 | | | | | | excellent |
| 37/49 | 1.0 | PEGMEA | 0.25 | 0.00045 | | | | | | excellent |
| 38[y] | 0.7 | PEGMEA | 0.25 | 0.00045 | | | | | | excellent |
| 39[yy] | 0.7 | PEGMEA | 0.25 | 0.00045 | | | | | | excellent |
| 40 | 0.3 | — | — | — | 33 | 89 | 0.08 | 335 | | |
| 41 | 0.5 | — | — | — | 34 | 92 | 0.09 | 735 | 25 | |
| 42 | 0.7 | — | — | — | 35 | 93 | 0.17 | 1120 | 49 | |
| 43 | 1.0 | — | — | — | 36 | 93 | 0.18 | 1530 | | |
| 44 | 2.0 | — | — | — | 38 | 94 | 0.25 | 3030 | 83* | |

[x]Reaction temperature 40° C.
[xx]Reaction temperature 60° C.
[xxx]Top Vision ™ LM GQ agarose (low-molecular-weight product)
[y]TBE buffer
[yy]Na-borate buffer
*Monomers: AA—acrylamide; VP—1-vinyl-2-pyrrolidinone; PEGA—poly(ethylene glycol) acrylate $M_n$ 375; PEGDA—poly(ethylene glycol) diacrylate $M_n$ 258; PEGMEMA1—poly(ethylene glycol) methyl ether methacrylate $M_n$ 300; PEGMEMA2—poly(ethylene glycol) methyl ether methacrylate $M_n$ 475; PEGMEMA3—poly(ethylene glycol) methyl ether methacrylate $M_n$ 2080; PEGMEA—poly(ethylene glycol) methyl ether acrylate $M_n$ 454.
**Optical density at 600 nm.
Relative strength - the ratio of the strength of a modified agarose gel to the strength of the standard agarose gel
Relative elasticity - the ratio of the weight deflecting standard agarose gel to the weight deflecting a modified agarose gel

The invention claimed is:

1. A method of preparing a gel for use in electrophoresis, which method comprises:
   (a) contacting agarose with a polymerisation initiator, the initiator forming a redox system with the agarose;
   (b) providing a mixture consisting essentially of the agarose resulting from step (a), one or more vinyl monomers, and a solvent, wherein the vinyl monomers are selected from the group consisting of poly(ethylene glycol) methyl ether acrylates and poly(ethylene glycol) methyl ether methacrylates;
   (c) exposing the mixture to polymerisation conditions to graft-polymerise the one or more monomers onto the agarose; and
   (d) allowing the mixture to form a gel.

2. A method according to claim 1, wherein the concentration of monomer in step (b) is 2% or less (w/v).

3. A method according to claim 2, wherein the concentration of monomer is in the range 0.25 to 1% (w/v).

4. A method according to claim 1, wherein the concentration of initiator in step (a) is 0.005% or less (w/v).

5. A method according to claim 4, wherein the concentration of initiator is in the range 0.0004 to 0.002% (w/v).

6. A method according to claim 1, which further comprises contacting the mixture with a reducing agent during or after step (c).

7. A method according to claim 6 wherein the reducing agent is dithiothreitol.

8. A method of preparing a gel for use in electrophoresis, which method comprises:
   (a) contacting agarose with a polymerisation initiator, the initiator forming a redox system with the agarose, wherein the initiator comprises cerium (4+);
   (b) providing a mixture consisting essentially of the agarose resulting from step (a), one or more vinyl monomers, and a solvent wherein the vinyl monomers are selected from the group consisting of poly(ethylene glycol) methyl ether acrylates and poly(ethylene glycol) methyl ether methacrylates;
   (c) exposing the mixture to polymerisation conditions to graft-polymerise the one or more monomers onto the agarose; and
   (d) allowing the mixture to form a gel.

9. A method according to claim 8, wherein the initiator is cerium (4+) ammonium nitrate.

10. A method according to claim 1, wherein the one or more vinyl monomers are non-ionic.

11. A method according to claim 1, wherein the one or more vinyl monomers are hydrophilic.

12. A method according to claim 1, wherein each monomer has a polyethylene glycol unit with a degree of polymerisation in the range 2 to 45.

13. A method according to claim 12, wherein each monomer has a polyethylene glycol unit with a degree of polymerisation in the range 2 to 20.

14. A method according to claim 12, wherein each monomer has a polyethylene glycol unit with a degree of polymerisation in the range 4 to 8.

15. A method according to claim 1, wherein the solvent is water.

16. A method according to claim 1, wherein the step of allowing the mixture to form a gel comprises cooling the mixture.

17. A gel for use in electrophoresis, which gel is obtainable from the method of claim 1.

18. A gel according to claim 17 for use in the separation of nucleic acids.

19. A method of preparing a gel for use in electrophoresis, which method comprises:
   (a) providing a mixture consisting essentially of a solvent, agarose, one or more vinyl monomers, wherein the vinyl monomers are selected from the group consisting of poly(ethylene glycol) methyl ether acrylates and poly(ethylene glycol) methyl ether methacrylates, and a polymerisation initiator, the initiator forming a redox system with agarose;
   (b) exposing the mixture to polymerisation conditions to graft-polymerise the one or more monomers onto the agarose; and
   (c) allowing the mixture to form a gel.

20. A method according to claim 19, wherein the concentration of monomer in step (a) is 2% or less (w/v).

21. A method according to claim 20, wherein the concentration of monomer is in the range 0.25 to 1% (w/v).

22. A method according to claim 19, wherein the concentration of initiator in step (a) is 0.005% or less (w/v).

23. A method according to claim 22, wherein the concentration of initiator is in the range 0.0004 to 0.002% (w/v).

24. A method according to claim 19, which further comprises contacting the mixture with a reducing agent during or after step (b).

25. A method according to claim 24 wherein the reducing agent is dithiothreitol.

26. A method of preparing a gel for use in electrophoresis, which method comprises:
   (a) providing a mixture consisting essentially of a solvent, agarose, one or more vinyl monomers, wherein the vinyl monomers are selected from the group consisting of poly(ethylene glycol) methyl ether acrylates and poly(ethylene glycol) methyl ether methacrylates and a polymerisation initiator, the initiator forming a redox system with agarose, wherein the initiator comprises cerium (4+);
   (b) exposing the mixture to polymerisation conditions to graft-polymerise the one or more monomers onto the agarose; and
   (c) allowing the mixture to form a gel.

27. A method according to claim 26, wherein the initiator is cerium (4+) ammonium nitrate.

28. A method according to claim 19, wherein the one or more vinyl monomers are non-ionic.

29. A method according to claim 19, wherein the one or more vinyl monomers are hydrophilic.

30. A method according to claim 19, wherein each monomer has a polyethylene glycol unit with a degree of polymerisation in the range 2 to 45.

31. A method according to claim 30, wherein each monomer has a polyethylene glycol unit with a degree of polymerisation in the range 2 to 20.

32. A method according to claim 30, wherein each monomer has a polyethylene glycol unit with a degree of polymerisation in the range 4 to 8.

33. A method according to claim 19, wherein the solvent is water.

34. A method according to claim 19, wherein the step of allowing the mixture to form a gel comprises cooling the mixture.

35. A gel for use in electrophoresis, which gel is obtainable from the method of claim 19.

36. A gel according to claim 35 for use in the separation of nucleic acids.

37. A kit for preparing a gel comprising graft copolymers for use in electrophoresis, said kit comprising:

(a) agarose;
(b) one or more vinyl monomers wherein the vinyl monomers are selected from the group consisting of poly(ethylene glycol) methyl ether acrylates and poly(ethylene glycol) methyl ether methacrylates;
(c) a polymerisation initiator capable of forming a redox system with agarose; and
(d) instructions for graft polymerizing the vinyl monomers to the agarose and preparing the gel.

38. A kit according to claim 37, wherein the initiator comprises cerium (4+).

39. A kit according to claim 37, wherein the one or more vinyl monomers are selected from non-ionic vinyl monomers and hydrophilic vinyl monomers.

40. A kit according to claims 37 which further comprises a reducing agent.

41. A kit according to claim 40, wherein the reducing agent is dithiothreitol.

42. A method of making a graft copolymer consisting essentially of a vinyl monomer and agarose, which method comprises:
    (a) providing:
        (i) agarose;
        (ii) one or more vinyl monomers, wherein the one or more monomers are selected from the group consisting of poly(ethylene glycol) methyl ether acrylates and poly(ethylene glycol) methyl ether methacrylates; and
        (iii) a polymerisation initiator capable of forming a redox system with agarose;
    (b) contacting the agarose with the initiator; and
    (c) graft-polymerising the one or more monomers onto the agarose.

43. A method according to claim 42, wherein the initiator comprises cerium (4+).

44. A method according to claim 43, wherein the initiator is cerium (4+) ammonium nitrate.

45. A method according to claim 42, wherein each monomer has a polyethylene glycol unit with a degree of polymerisation in the range 2 to 45.

46. A method according to claim 45, wherein each monomer has a polyethylene glycol unit with a degree of polymerisation in the range 2 to 20.

47. A method according to claim 45, wherein each monomer has a polyethylene glycol unit with a degree of polymerisation in the range 4 to 8.

48. A method according to claim 42, wherein the graft-polymerisation is carried out in a solvent, and wherein the concentration of monomer in the solvent is 2% or less (w/v).

49. A method according to claim 48, wherein the concentration of monomer is in the range 0.25 to 1% (w/v).

50. A method according to claim 42, wherein the polymerisation is carried out in a solvent, and wherein the concentration of initiator in the solvent is 0.005% or less (w/v).

51. A method according to claim 50, wherein the concentration of initiator is in the range 0.0004 to 0.002% (w/v).

52. A method according to claim 48, wherein the solvent is water.

53. A method according to claim 50, wherein the solvent is water.

54. An isolated graft copolymer obtainable from the method of claim 42.

55. A gel for use in electrophoresis, which gel comprises a graft copolymer obtainable from the method of claim 42.

56. A gel according to claim 55 for use in the separation of nucleic acids.

57. A kit for preparing a gel for use in electrophoresis, said kit comprising a graft copolymer obtainable from the method of claim 42.

58. A method of preparing comprising graft copolymers for use in electrophoresis, which method comprises:
    (a) contacting agarose with a polymerisation initiator, the initiator forming a redox system with the agarose;
    (b) providing a mixture comprising the agarose resulting from step (a), one or more vinyl monomers, and a solvent, wherein the vinyl monomers are selected from the group consisting of poly(ethylene glycol) methyl ether acrylates and poly(ethylene glycol) methyl ether methacrylates;
    (c) exposing the mixture to polymerisation conditions to graft-polymerise the one or more monomers onto the agarose; and
    (d) allowing the mixture to form a gel comprising graft copolymers, wherein the graft copolymers consist of the graft coplymers of step (c).

59. The method of claim 58 wherein the concentration of initiator in step (a) is 0.005% or less (w/v) and wherein the concentration of monomer in step (b) is 2% or less (w/v).

* * * * *